(12) United States Patent
Zeidler et al.

(10) Patent No.: US 6,488,939 B1
(45) Date of Patent: Dec. 3, 2002

(54) CLEAVABLE SOLID DOSAGE FORMS AND METHOD FOR THE PRODUCTION THEREOF

(75) Inventors: Jürgen Zeidler, Mutterstadt (DE); Jörg Rosenberg, Ellerstadt (DE); Werner Maier, Schifferstadt (DE); Jörg Neumann, Limburgerhof (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/857,018

(22) PCT Filed: Dec. 3, 1999

(86) PCT No.: PCT/EP99/09463

§ 371 (c)(1),
(2), (4) Date: May 31, 2001

(87) PCT Pub. No.: WO00/33786

PCT Pub. Date: Jun. 15, 2000

(30) Foreign Application Priority Data

Dec. 4, 1998 (DE) .......................... 198 56 147

(51) Int. Cl.⁷ ............................. A61K 9/00; A61K 9/20
(52) U.S. Cl. ....................................... 424/400; 424/464
(58) Field of Search .................................. 424/400, 464

(56) References Cited

U.S. PATENT DOCUMENTS

| | | | |
|---|---|---|---|
| 3,927,194 A | 12/1975 | Geller | 424/15 |
| 4,353,887 A | 10/1982 | Hess et al. | 424/15 |
| 4,735,805 A * | 4/1988 | Ni et al. | 424/464 |
| 5,562,920 A | 10/1996 | Demmer et al. | 424/464 |
| 6,009,690 A | 1/2000 | Rosenberg et al. | 53/454 |

FOREIGN PATENT DOCUMENTS

| | | |
|---|---|---|
| CN | 683 066 | 1/1994 |
| JP | 08 277 217 | 10/1996 |

OTHER PUBLICATIONS

H.G. Kristensen et al. "Mass Uniformity of Tablets Broken by Hand" Pharmeuropa vol. 7 No. 2, Jun. 1995 pp. 298–302.

* cited by examiner

*Primary Examiner*—Alton Pryor
(74) *Attorney, Agent, or Firm*—Keil & Weinkauf

(57) ABSTRACT

Solid, elongate dosage forms (10) with a long axis (11) and with a length (L) which is defined by projection of the ends (12, 13) of the dosage form to the long axis, where a cross-sectional area (14, 15, 16) oriented perpendicular to the long axis (11) has an area which is variable along the long axis (11) and increases from a cross-sectional area (15) which is located between the ends (12, 13) and has a minimal area essentially continuously toward the two ends (12, 13) up to in each case a cross-sectional area (14 and 16 respectively) with a maximal area, wherein the distance of the maximal cross-sectional area (14) which is located near one end (12) from the maximal cross-sectional area (16) which is located near the other end (13) is, projected on the long axis (11), more than half the length (L) of the dosage form (10), are described.

10 Claims, 2 Drawing Sheets

CLEAVABLE SOLID DOSAGE FORMS AND METHOD FOR THE PRODUCTION THEREOF

This application is a 371 of PCT/EP99/09403 filed Dec. 3, 1999.

The present invention relates to divisible solid dosage forms, in particular solid pharmaceutical dosage forms, and to a process for their production.

It is often desirable for solid pharmaceutical dosage forms, for example tablets, to be divisible in order to be able to alter the dosage without the need to produce individual tablets for each particular dosage. Division of a tablet into accurately predetermined parts makes it possible to administer a fraction or any multiple of the fraction of the active ingredient present in the tablet.

To facilitate division, tablets normally have scores. The tablet is broken apart by exerting pressure on the tablet, with the tablet being held between two fingers or with both hands. Divisible tablets are described, for example, in CH 683 066 or U.S. Pat. No. 3,927,194.

DE-B 30 30 622 describes a divisible tablet with controlled and delayed release of active ingredient. The ratio of length to width to height in this case is intended to be about 2.5–5:about 0.9–2:1. One or more relatively deep score(s) running perpendicular to the length and to the height are present. The bottom and top surfaces are, independently of one another, flat or curved convexly around the long axis or parallels thereto.

DE-B 44 46 470 describes a process for producing divisible tablets by shaping an active ingredient-containing melt in a calender with two counter-rotating molding rolls which have depressions for receiving and molding the melt to tablets, where the depressions are divided by at least one bar which extends essentially as far as the surface of the molding roll and forms a score.

One problem with the known divisible solid dosage forms is that expenditure of a relatively large force is necessary to divide the dosage forms. This problem is particularly pronounced with dosage forms produced by melt extrusion because they usually consist of a very hard and brittle material. Attempts have been made to bypass this problem by providing the solid dosage forms with very deep notches with large notch angles. However, with these approaches to a solution there is the risk that the solid dosage form will break during after-treatment steps, e.g. during deflashing or film-coating, due to the stress on the material, which leads to a large proportion of rejects.

A further serious problem with known divisible solid dosage forms is the inadequate uniformity of mass of the manually divided halves of the dosage forms. Corresponding investigations have revealed standard deviations of between 3 and 13% for the tablet halves (see H. G. Kristensen et al., Pharmeuropa, Volume 7, No. 2, June 1995, pp. 298 et seq.). Standard deviations as high as this lead to inaccurate dosages, which is particularly undesirable with active ingredients of high activity. The inadequate uniformity of mass of the manually divided tablet halves derives, on the one hand, from the fractures area not being exactly at the intended place and, on the other hand, from the tendency of the tablet material to escape at outer edges of the tablet mold, which leads to losses of active ingredient.

It is an object of the present invention to provide solid dosage forms which display easy divisibility and, at the same time, a sufficient resistance to stress for further processing steps. It was additionally intended that the solid dosage forms be of a nature such that the fragments resulting from manual division of the solid dosage forms display a maximum uniformity of mass.

We have found that this object is achieved by the solid dosage forms having a particular geometry. The present invention therefore relates to a solid, elongate dosage form (10) with a long axis (11) and with a length (L) which is defined by projection of the ends (12, 13) of the dosage form onto the long axis, where a cross-sectional area (14, 15, 16) oriented perpendicular to the long axis (11) has an area which is variable along the long axis (11) and increases from a cross-sectional area (15) which is located between the ends (12, 13) and has a minimal area essentially continuously toward the two ends (12, 13) up to in each case a cross-sectional area (14 and 16 respectively) with a maximal area, wherein the distance of the maximal cross-sectional area (14) which is located near one end (12) from the maximal cross-sectional area (16) which is located near the other end (13) is, projected on the long axis (11), more than half the length (L) of the dosage form (10).

Figure 1:
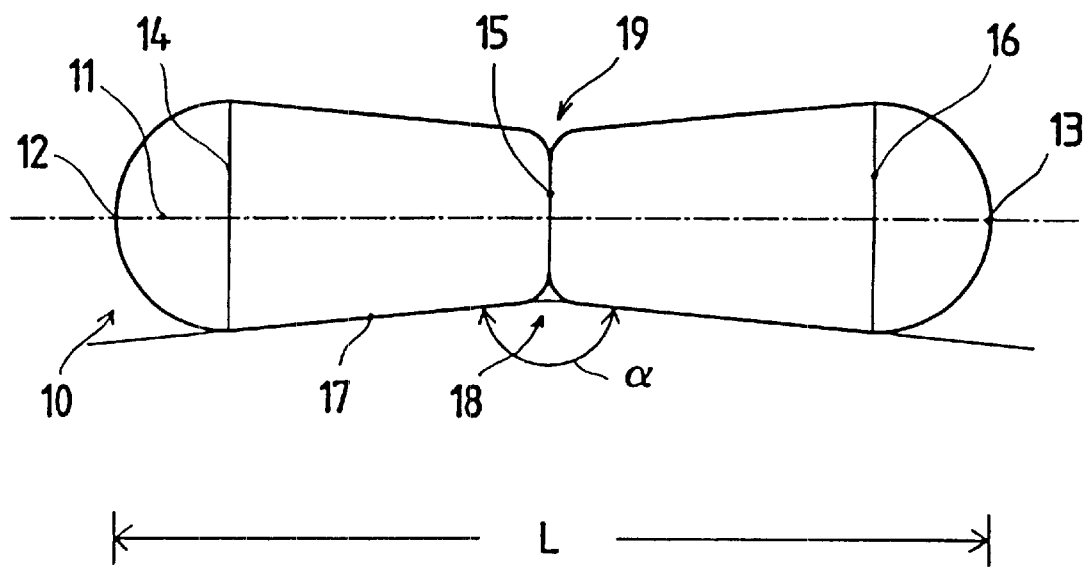
FIG. 1 shows a dosage form according to the invention in cross section.

The long axis referred to here is the principal axis of inertia of the solid dosage form on which the projection of the dosage form has the greatest extent. This extent is referred to hereinafter as the length (L) of the dosage form. The extents of the projections of the dosage form onto the two other principal axes of inertia correspond respectively to the height and width of the dosage form. "Elongate" means that the length of the dosage form is larger than its width or its height. The length of the dosage form is preferably more than 2.5 times, in particular 3 to 4.5 times, the width or height. The cross-sectional area means for the purposes of the present invention the area included by the intersection line of the outer surface of the dosage form on a plane oriented perpendicular to the long axis of the solid dosage form. The two cross-sectional areas with maximal area lie opposite to one another at a distance of more than half the length of the dosage form in relation to the cross-sectional areas with minimal area. The dosage forms according to the invention may have, for example at the level of the minimal cross-sectional area, an all-round "constriction". Alternatively, a notch may be present on only one side of the tablet, whereas the opposite side is flat. A further possibility is for dosage forms according to the invention to be provided with notches on opposite sides.

With the dosage forms according to the invention there is normally a reduction again in the area of the cross-sectional area toward one or both ends after reaching the maximal cross-sectional area. However, the area may also remain constant at this maximum value as far as the two ends of the dosage form after reaching the maximal cross-sectional area. In particular embodiments, the maximal cross section is reached only at the ends of the dosage form.

The shape of the dosage form according to the invention makes it possible to grip the dosage form satisfactorily with both hands. The elongate shape with the outer-lying centers of mass results in a favorable torque action which facilitates division of the dosage forms. Because the cross-sectional area along which division of the dosage form takes place is small, little "work for breaking" is necessary. The dosage forms according to the invention can be divided into fragments of accurately predetermined size. This achieves satisfactory uniformity of mass of the manually divided fragments of the dosage forms according to the invention with a small standard deviation. The dosage forms according to the invention can also be further processed very well without breaking. Because of the mass distribution predetermined by the shape of the dosage forms according to the invention, the dosage forms are substantially stable to axial stress and to lateral impact.

Preferred solid dosage forms according to the invention are those where the area of the minimal cross-sectional area (15) is no more than two thirds, in particular no more than 0.6 times the area of the maximal cross-sectional area.

The most important application of the present invention is for solid dosage forms which can be halved. With these dosage forms the minimal cross-sectional area is located in a plane of symmetry of the dosage form.

In preferred dosage forms according to the invention, at least one line running on the surface of the dosage form in the longitudinal direction displays a kink at the level of the minimal cross-sectional area. This defines the place where the dosage form is intended to break more accurately. As a measure for the kink it is possible to define a notch angle which corresponds to the angle included by the two tangential planes placed on the surface of the dosage form on both sides of the minimal cross-sectional area. Preferred dosage forms according to the invention have a notch angle of more than 90°, in particular of more than 100°. The notch angle is generally less than 170°, preferably less than 162°. Any score which is present, as discussed hereinafter, is not taken into account here.

It has been found that when breaking open dosage forms the tablet material tends to break at sharp edges. Preferred dosage forms according to the invention therefore have essentially rounded edges. It is particularly preferred for the dosage forms according to the invention to have essentially no fillet in their equator. It is possible in this way to minimize losses of active ingredient on manual division of the dosage forms.

For further facilitating divisibility, a score can be formed in the surface of the dosage form according to the invention along the periphery or along sections of the periphery of the minimal cross-sectional area. The depth of the score is preferably small compared with the depth of the constriction or of the notch caused by the difference in the cross-sectional areas.

Solid dosage forms according to the invention can be produced by any suitable process. However, it is particularly preferred for the dosage forms to be produced by a melt calendering. Melt calendering makes it possible to produce dosage forms which have no pronounced fillet on the tablets. The fillet on tablets produced by conventional compression refers to the area formed by the wall of the die.

In melt calendering, at least one polymeric binder, at least one active ingredient and, where appropriate, conventional additives are mixed to form a plastic mixture, and this mixture is shaped in a calender with two counter-rotating molding rolls. At least one of the molding rolls has depressions to receive and shape the plastic mixture to dosage forms, and the depressions are designed so that solid dosage forms according to the above definition are obtained.

The dosage forms according to the invention generally comprise:

A) 0.1 to 90% by weight, in particular 0.1 to 60% by weight (based on the total weight of the dosage form), of an active ingredient, b) 10 to 99.9% by weight, in particular 40 to 99.9% by weight, of a binder, preferably polymeric binder and c) where appropriate additives.

Suitable polymeric binders are polymers, copolymers, cellulose derivatives, starch and starch derivatives, for example: polyvinylpyrrolidone (PVP), copolymers of N-vinylpyrrolidone (NVP) and vinyl acetate or vinyl propionate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, polyacrylamides, polyethylene glycols, polyvinylformamide (partially or totally hydrolyzed where appropriate), cellulose esters, cellulose ethers, especially methylcellulose and ethylcellulose, hydroxyalkylcelluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, and mannans, especially galactomannans. Of these, polyvinylpyrrolidone, copolymers of N-vinylpyrrolidone and vinyl esters, poly(hydroxyalkyl acrylates), poly(hydroxyalkyl methacrylates), polyacrylates, polymethacrylates, alkylcelluloses and hydroxyalkylcelluloses are particularly preferred.

The polymeric binder must soften or melt in the complete mixture of all the components in the range from 50 to 180° C., preferably 60 to 130° C. The glass transition temperature of the mixture must therefore be below 180° C, preferably below 130° C. If necessary, it is reduced by conventional pharmacologically acceptable plasticizing auxiliaries. The amount of plasticizer does not exceed 30% by weight, based on the total weight of binder and plasticizer, in order to form drug forms which are stable on storage and show no cold flow. However, the mixture preferably contains no plasticizer.

Examples of such plasticizers are:

long chain alcohols, ethylene glycol, propylene glycol, glycerol, trimethylolpropane, triethylene glycol, butanediols, pentanols such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol monoacetate, glycerol diacetate or glycerol triacetate or sodium diethyl sulfosuccinate. The concentration of plasticizer is generally from 0.5 to 15, preferably 0.5 to 5, % of the total weight of the mixture.

Conventional pharmaceutical excipients, whose total amount can be up to 100% of the weight of the polymer, are, for example, extenders and bulking agents such as silicates or diatomaceous earth, magnesium oxide, aluminum oxide, titanium oxide, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % of the total weight of the mixture.

Mold release agents such as magnesium, zinc and calcium stearates, sodium stearylfumarate, talc and silicones, in a concentration of from 0.1 to 5, preferably 0.1 to 3, % of the total weight of the mixture. Also suitable as mold release agents are animal or vegetable fats, especially in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, especially lecithin. The mono- and diglycerides are preferably derived from the abovementioned fatty acid types. The total amount of fats, waxes, mono-, diglycerides and/or lecithins is from 0.1 to 30, preferably 0.1 to 5, % of the total weight of the composition for the particular layer;

flowability agents such as Aerosil (highly disperse silica) or talc;

dyes such as azo dyes, organic or inorganic pigments or dyes of natural origin, with preference for inorganic pigments in a concentration of from 0.001 to 10, preferably 0.5 to 3, % of the total weight of the mixture;

stabilizers such as antioxidants, light stabilizers, hydroperoxide destroyers, radical scavengers, stabilizers against microbial attack.

It is also possible to add wetting agents, preservatives, disintegrants and adsorbents, (cf., for example, H. Sucker et al., Pharmazeutische Technologie, Thieme-Verlag, Stuttgart 1978).

Excipients include for the purpose of the invention substances for producing a solid solution of the active ingredient. Examples of these auxiliaries are pentaerythritol and pentaerythritol tetraacetate, polymers such as polyethylene oxide and polypropylene oxide and their block copolymers (poloxamers), phosphatides such as lecithin, homo- and copolymers of vinylpyrrolidone, surfactants such as polyoxyethylene 40 stearate, and citric and succinic acids, bile acids, sterols and others as indicated, for example, in J. L. Ford, Pharm. Acta Helv. 61 (1986) pp.69–88.

Pharmaceutical excipients are also regarded as being additions of bases and acids to control the solubility of an active ingredient (see, for example, K. Thoma et al., Pharm. Ind. 51 (1989) 98–101).

The only preconditions for the suitability of excipients are adequate temperature stability and adequate compatibility of the excipient with the active ingredient.

Active ingredients mean for the purpose of the invention all substances with a pharmaceutical effect and minimal side effects as long as they do not completely decompose under the processing conditions. They are, in particular, active pharmaceutical ingredients (for humans and animals), active ingredients for plant treatment, insecticides, active ingredients for human and animal food, fragrances and perfume oils. The amount of active ingredient per dose unit and the concentration may vary within wide limits depending on the activity and the release rate. The only condition is that they suffice to achieve the desired effect. Thus, the concentration of active ingredient can be in the range from 0.1 to 95, preferably from 20 to 80, in particular 30 to 70, % by weight. It is also possible to employ active ingredient combinations. Active ingredients for the purpose of the invention also include vitamins and minerals. The vitamins include the vitamins of the A group, the B group, which are meant besides $B_1$, $B_2$, $B_6$ and $B_{12}$ and nicotinic acid and nicotinamide to include also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Plant treatment agents include, for example vinclozolin, apoxiconazole and quinmerac.

The process according to the invention is suitable, for example, for processing the following active ingredients:

acebutolol, acetylcysteine, acetylsalicylic acid, acyclovir, alfacalcidol, allantoin, allopurinol, alprazolam, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefadroxil, cefalexin, cefazolin, cefixime, cefotaxime, ceftazidime, ceftriaxone, cefuroxime, chloramphenicol, chlorhexidine, chlor-pheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxocyclin, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin-mononucleotide, fluconazole, flunarizine, fluorouracil, fluoxetine, flurbiprofen, folinic acid, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium-hydroxide, ibuprofen, imipenem, imipramine, indomethacin, iohexol, iopamidol, isosorbide-dinitrate, isosorbide-mononitrate, isotretinoin, itraconazole, ketotifen, ketoconazole, ketoprofen, ketorolac, labetalol, lactulose, lecithin, levocarnitine, levodopa, levoglutamide, levonorgestrel, levothyroxine, lidocaine, lipase, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multi-vitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, pentoxifylline, phenobarbital, phenoxymethylpenicillin, phenylephrine, phenylpropanolamine, phenytoin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, selegiline, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone-acetonide, triamterene, trimethoprim, troxerutin, uracil, valproic acid, vancomycin, verapamil, vitamin E, zidovudine.

Preferred active ingredients are ibuprofen (as racemate, enantiomer or enriched enantiomer), metoprolol, ketoprofen, flurbiprofen, acetylsalicylic acid, verapamil, paracetamol, nifedipine or captopril.

To produce the solid dosage forms, a plastic mixture of the components (melt) is prepared and then subjected to a shaping step. There are various ways of mixing the components and forming the melt. The mixing can take place before, during and/or after the formation of the melt. For example, the components can be mixed first and then melted or be mixed and melted simultaneously. The plastic mixture is often then homogenized in order to disperse the active ingredient thoroughly.

However, it has proven preferable, especially when sensitive active ingredients are used, first to melt the polymeric binder and, where appropriate, make a premix with conventional pharmaceutical additives, and then to mix in (homogenize), the sensitive active ingredient(s) in the plastic phase in intensive mixers with very short residence times. The active ingredient(s) can for this purpose be employed in solid form or in solution or dispersion.

The components are generally employed as such in the production process. However, they can also be used in liquid form, i.e. as solution, suspension or dispersion.

Suitable solvents for the liquid form of the components are primarily water or a water-miscible organic solvent or a mixture thereof with water. However, it is also possible to use organic solvents which are immiscible or miscible with water. Suitable water-miscible solvents are, in particular, $C_1$–$C_4$-alkanols, such as ethanol, isopropanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chloride, and aromatic hydrocarbons such as toluene and xylene. Another solvent which can be used is liquid $CO_2$.

The solvent used in the individual case depends on the component to be taken up and its properties. For example, pharmaceutical active ingredients are frequently used in the form of a salt which is generally soluble in water. Water-soluble active ingredients can therefore be employed as aqueous solution or, preferably, be taken up in the aqueous solution or dispersion of the binder. The same applies to active ingredients which are soluble in one of the solvents mentioned, if the liquid form of the components used is based on an organic solvent.

It is possible where appropriate to replace melting by dissolving, suspending, or dispersing in the abovementioned solvents, if required and/or necessary with addition of suitable excipients such as emulsifiers. The solvent is then generally removed to form the melt in a suitable apparatus, for example an extruder. This will be comprised by the term mixing hereinafter.

The melting and/or mixing takes place in an apparatus customary for this purpose. Particularly suitable ones are extruders or containers which can be heated where appropriate and have an agitator, for example kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986.

A particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (for example ORP, CRP, AP, DTB supplied by List or Reactotherm supplied by Krauss-Maffei or Ko-Kneader supplied by Buss), trough mixers and internal mixers or rotor/stator systems (for example Dispax supplied by IKA).

In the case of sensitive active ingredients it is preferable first for a polymeric binder to be melted in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, for example via a weigh feeder. Plastic compositions can be fed in directly from an extruder or via a gear pump, which is particularly advantageous if the viscosities and pressures are high. Liquid media can be metered in by a suitable pump unit.

The mixture obtained by mixing and/or melting the binder, the active ingredient and, where appropriate, the additive(s) ranges from pasty to viscous (plastic) or fluid and is therefore extrudable. The glass transition temperature of the mixture is below the decomposition temperature of all the components present in the mixture. The binder should preferably be soluble or swellable in a physiological medium.

The steps of mixing and melting in the process can be carried out in the same apparatus or in two or more separately operating apparatuses. The preparation of a premix can take place in one of the conventional mixing apparatuses described above. A premix of this type can then be fed directly, for example, into an extruder and subsequently be extruded, where appropriate with the addition of other components.

It is possible in the process according to the invention to employ as extruders single screw machines, intermeshing screw machines or else multiscrew extruders, especially twin screw extruders, corotating or counter-rotating and, where appropriate, equipped with kneading disks. If it is necessary in the extrusion to evaporate a solvent, the extruders are generally equipped with an evaporating section. Particularly preferred extruders are those of the ZSK series from Werner & Pfleiderer.

The resulting mixture is preferably solvent-free, i.e. it contains neither water nor an organic solvent.

The plastic mixture is subjected to a shaping in a calender with counter-rotating molding rolls. The molding rolls have on their surfaces depressions suitable for receiving and shaping the plastic mixture. The plastic mixture is in this case introduced into the trough-like space between the molding rolls, for example by means of a filling wedge. Two depressions corresponding to one another on the molding rolls briefly meet at the contact line of the molding rolls to form a tablet mold. As rotation continues, the depressions diverge again and release the molded dosage form. The depressions on the molding rolls are designed so that they correspond to the negative mold for one "half" of the dosage forms according to the invention. Depressions corresponding to one another on the molding rolls may have the same shape or differ in shape. The depressions on one molding roll may have a uniform depth, whereas the depressions on the other molding roll have different depths along the long axis thereof. Alternatively, depressions in both molding rolls may have varying depths along the long axes. It is preferred for the long axis of the depressions to be parallel to the axis of rotation of the molding rolls.

The resulting dosage forms can in a subsequent step be rounded, deflashed and/or provided with a coating by conventional processes. Suitable materials for film coatings are film formers, e.g. polyacrylates such as the Eudragit types, cellulose esters such as the hydroxypropylcellulose phthalates, and cellulose ethers such as ethylcellulose, hydroxypropylmethylcellulose or hydroxypropylcellulose, where appropriate mixed with bulking agents, coloring pigments, wetting agents and plasticizers.

It is specifically possible for solid solutions to be formed. The term "solid solutions" is familiar to the skilled worker, for example from the literature cited at the outset. The active ingredient in solid solutions of active ingredients in polymers is in the form of a molecular dispersion in the polymer.

The figures and the example hereinafter are intended to explain the invention in detail.

FIG. 1 shows a cross section of a dosage form according to the invention. The dosage form (10) has a long axis (11) and two ends (12, 13). A first maximal cross-sectional area (14) is located near one end (12) and a second maximal cross-sectional area (16) is located near the other end (13). A cross-sectional area (15) with minimal cross section is located in the center of the tablet. The surface plane (17) lying in the plane of the drawing has a kink (18) at the level of the minimal cross-sectional area (15). The tangential planes placed on the surface of the dosage form on both sides of the minimal cross-sectional area (15) include a notch angle (a). The depicted dosage form additionally has a score (19).

EXAMPLES

Example 1

A pharmaceutical mixture was prepared in accordance with the following formula:

| | |
|---|---|
| Verapamil HCl | 48.0% by weight; |
| Hydroxypropylcellulose | 31.5% by weight; |
| Hydroxypropylmethylcellulose | 17.5% by weight; |
| Lecithin | 3.0% by weight. |

The pharmaceutical mixture was extruded in a twin-screw extruder under the following conditions:

| | |
|---|---|
| Temperature range | 80–125° C. |
| Screw speed | 120 rpm |
| Vacuum | 100 mbar |
| Melt flow rate | 120 kg/h |

Figure 2:
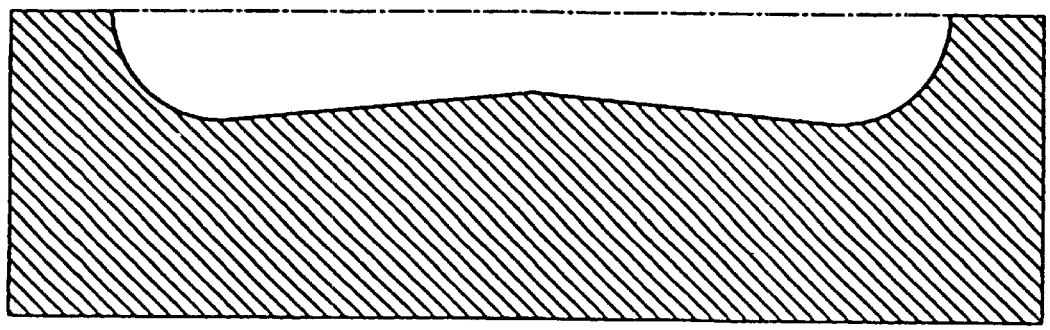
FIG. 2 shows a depression in the molding roll of a molding calender with which the dosage forms according to the invention can be obtained.
Figure 3:
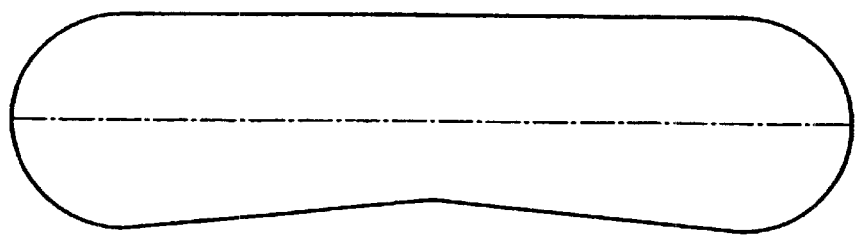
FIG. 3 shows a dosage form according to the invention which can be obtained using a molding roll with depressions of the type shown in FIG. 2.

The melt was passed into a molding calender with two molding rolls. One of the molding rolls had depressions of the type shown in FIG. 2 on its surface. The second molding roll had on its surface elongate depressions with a corresponding outline and a uniform depth. This resulted in tablets as depicted in FIG. 3. They could be broken into two equal halves easily and smoothly. The measured standard deviations for the manually divided dosage forms were in the region of 2% for a total mass of 500 mg for the dosage forms. The standard deviation thus achieved is in a pharmaceutically acceptable range.

We claim:

1. A solid, elongate dosage form with a long axis and with a length which is defined by projection of the ends of the dosage form onto the long axis, where a cross-sectional area oriented perpendicular to the long axis has an area which is variable along the long axis and increases from a cross-sectional area which is located between the ends up to in each case a cross-sectional area which is located near one end from the maximal cross-sectional area which is located near the other end is, projected on the long axis, more than half the length of the dosage from, and wherein the dosage from has no fillet in its equator.

2. A dosage form as claimed in claim 1, wherein the distance of the maximal cross-sectional area located near one end from the maximal cross-sectional area located near the other end is, projected on the long axis, more than 0.6 times the length.

3. A dosage form as claimed in claim 1, wherein the area of the minimal cross-sectional area is not more than two thirds of the area of the maximal cross-sectional area.

4. A dosage form as claimed in claim 3, wherein the area of the minimal cross-sectional area is no more than 0.6 times the area of the maximal cross-sectional area.

5. A dosage form as claimed in claim 1, wherein the minimal cross-sectional area lies in a plane of symmetry of the dosage form.

6. A dosage form as claimed in claim 1, wherein at least one surface line running in the longitudinal direction on the dosage form has a kink at the level of the minimal cross-sectional area.

7. A dosage form as claimed in claim 6, wherein the dosage form has a notch angle of more than 90°.

8. A dosage form as claimed in claim 1, which has rounded edges.

9. A dosage form as claimed in claim 1, wherein a score is formed in the surface of the dosage form along the periphery or along sections of the periphery of the minimal cross-sectional area.

10. A process for producing dosage forms by molding an active ingredient-containing melt in a calender with two counter-rotating molding rolls, of which at least one has depressions to receive and shape the melt to dosage forms, wherein the molding roll(s) has (have) depressions designed so that dosage forms as claimed in claim 1 are obtained.

* * * * *